United States Patent [19]

Waller

[11] 4,416,801
[45] Nov. 22, 1983

[54] TOLUIC ACID

[75] Inventor: Francis J. Waller, Wilmington, Del.

[73] Assignee: E. I. Du Pont de Nemours & Co., Wilmington, Del.

[21] Appl. No.: 409,716

[22] Filed: Aug. 19, 1982

Related U.S. Application Data

[60] Division of Ser. No. 215,712, Dec. 15, 1980, Pat. No. 4,356,318, which is a continuation-in-part of Ser. No. 174,920, Aug. 4, 1980, abandoned, which is a continuation-in-part of Ser. No. 108,819, Dec. 31, 1979, abandoned.

[51] Int. Cl.$^3$ ............................................. B01J 31/06
[52] U.S. Cl. ..................................... 502/153; 502/169
[58] Field of Search .......................... 252/431 R, 429 R

[56] References Cited

U.S. PATENT DOCUMENTS

| | | | |
|---|---|---|---|
| 3,282,875 | 11/1966 | Connolly et al. | 260/29.6 |
| 3,700,729 | 10/1972 | Fenton | 260/515 R |
| 3,917,670 | 3/1972 | Baird, Jr. et al. | 260/471 R |
| 3,920,734 | 11/1975 | Ichikawa et al. | 260/515 R |
| 3,987,058 | 10/1976 | Saunders et al. | 252/431 R X |
| 4,038,213 | 7/1977 | McClure et al. | 252/430 |
| 4,093,647 | 8/1977 | van Venrooy | 260/515 R |
| 4,100,359 | 1/1977 | Schmerling et al. | 560/232 |
| 4,188,308 | 2/1980 | Vaughan | 252/431 R X |
| 4,303,551 | 12/1981 | Vaughan | 252/430 |

FOREIGN PATENT DOCUMENTS 5569 11/1979 European Pat. Off. .
2340592 2/1974 Fed. Rep. of Germany .
1485816 9/1977 United Kingdom .

OTHER PUBLICATIONS

Japanese abstract J5 1146-430, 12/76.
Chem. Systems, Inc., Process Evaluation and Research Planning Report, 2nd Quarter 1976.
Fujiwara et al., J. Chem. Soc. Chem. Communications No. 5, 220 (1980).
Olah and Meidar, Synthesis, 671 (1978).
Kelly et al., Du Pont Innovation 4 (2), 4, (1973).
Du Pont Product Information Bulletin E–05569, (Feb. 1976).
Rubenstein and Bard, J. Am. Chem. Soc., 102, 6641, (1980).
Olah, Prakash and Sommer, Science, 206, 13, (1979).
Olah, Kaspi and Bukala, J. Org. Chem., 42, 4187, (1977).
Kaspi and Olah, J. Org. Chem., 43, 3142, (1978).
Kaspi, Montgomery and Olah, J. Org. Chem., 43, 3147, (1978).
Gramstad and Haszeldine, J. Chem. Soc., 173, (1956).
Haszeldine and Kidd, J. Chem. Soc., 4228, (1954).
Batchelor et al., Inorg. Chem., 16, 1414, (1977).

*Primary Examiner*—Patrick Garvin

[57] ABSTRACT

Process for oxidatively carbonylating toluene to toluic acid, at least 50 mol % of the toluic acid being the p-isomer, said process comprising contacting and reacting, at 110°–250° C., at a pressure of at least 500 psi (3.45 MPa), toluene, carbon monoxide, oxygen and the catalyst ingredients consisting essentially of (a) a compound of rhodium, iridium, ruthenium, platinum, palladium or osmium;
(b) a sulfur oxy-acid or a Group Ia or IIa metal salt of a sulfur oxy-acid; and
(c) an acid or acid mixture having a Hammett acidity value ($-H_o$) of greater than 7.0, said catalyst ingredients containing 0.5–30 mol % of (a) and 70–99.5 mol % of (b+c), with the molar ratios of (b/a) and (c/a) each being at least 2, and recovering toluic acid.

3 Claims, No Drawings

TOLUIC ACID

CROSS-REFERENCE TO RELATED APPLICATIONS

This is a division of application Ser. No. 215,712 filed Dec. 15, 1980, now U.S. Pat. No. 4,356,318, as a continuation-in-part of application Ser. No. 174,920, filed Aug. 4, 1980, which is a continuation-in-part of application Ser. No. 108,819, filed Dec. 31, 1979. The two earliest filed applications have been abandoned.

DESCRIPTION

TECHNICAL FIELD

This invention relates to the oxidative carbonylation of aromatic compounds, for example, the preparation of toluic acids from toluene, carbon monoxide and oxygen.

BACKGROUND

The oxidative carbonylation of aromatic compounds to aromatic carboxylic acids is well known in the art. U.S. Pat. No. 3,700,729 discloses the catalytic liquid phase process comprising contacting an aromatic compound and carbon monoxide in a substantially anhydrous organic liquid reaction medium which is inert to the reactants and the catalyst which is a halide salt of a Group VIII metal in its highest oxidation state, continuing the contacting until the catalyst is reduced to a lower valence state and the aromatic compound is oxidatively carbonylated, and thereafter hydrolyzing the carbonylated compound to the aromatic carboxylic acid. The patent exemplifies the conversion of toluene to p-toluic acid. U.S. Pat. No. 3,920,734 discloses a process for preparing an aromatic carboxylic acid from an aromatic compound by means of carbon monoxide, oxygen and a palladium carboxylate catalyst. The patent exemplifies the conversion of toluene to a mixture of toluic acid isomers. U.S. Pat. No. 4,093,647 discloses a process for preparing an aromatic carboxylic acid from an aromatic compound of the benzene series by means of carbon monoxide and an inorganic salt mixture consisting of a major amount of a thallium salt and a minor amount of a palladium salt. The patent exemplifies the formation of a mixture of toluic acid isomers, predominantly the p-isomer, from toluene.

The acid-catalyzed carbonylation of aromatic compounds to form aldehydes is known in the art. Chem Systems, Inc., Process Evaluation and Research Planning Report, 2nd quarter, 1976, discloses the $HF/BF_3$ catalyzed carbonylation of toluene to tolualdehyde which can be converted to terephthalic acid by a liquid phase oxidation. A similar disclosure as to the formation of tolualdehyde is made in British Pat. No. 1,485,816. Japanese Publication No. J5 1146-430 based on Japanese Patent application No. 070587 discloses the formation of tolualdehyde from the reaction of toluene and carbon monoxide in the presence of trifluoromethanesulfonic acid (often referred to as triflic acid) in an anhydrous state or in combination with a Lewis acid.

It is an object of this invention to provide a catalytic liquid phase process for producing toluic acids from toluene. A further object is to provide such a process whereby at least 50 mol % of the toluic acids produced is p-toluic acid. Other objects will become apparent hereinafter.

DISCLOSURE OF INVENTION

For further comprehension of the invention, and of the objects and advantages thereof, reference may be made to the following description and to the appended claims in which the various novel features of the invention are more particularly set forth.

The invention resides in a process for preparing toluic acids, at least 50 mol % of which is p-toluic acid, by means of a catalytic oxidative carbonylation reaction from toluene, oxygen and carbon monoxide. More specifically, the process of the invention resides in contacting and reacting toluene, carbon monoxide, oxygen and the catalyst ingredients consisting essentially of (a) a compound of rhodium, iridium, ruthenium, platinum, palladium or osmium;
(b) a sulfur oxy-acid or a Group Ia or IIa metal salt of a sulfur oxy-acid; and
(c) an acid or acid mixture having a Hammett acidity value ($-H_o$) of greater than 7.0, said catalyst ingredients containing 0.5–30 mol % of (a) and 70–99.5 mol % of (b+c), with the molar ratios (b/a) and (c/a) each being at least 2, preferably at least 3, most preferably at least 4, and recovering toluic acid.

Included under (c) are strong sulfur oxy-acids such as, for example, sulfuric acid ($-H_o$ of 11), oleum and certain sulfonic acids which are also suitable for use under (b). Although not wishing to be bound by this explanation, it is thought that the active catalyst for the oxidative carbonylation reaction consists of one or more ionic species of sulfate or sulfonate of an above-listed Group VIII metal, formed by the partial or complete replacement of the anions or ligands of the starting Group VIII metal compound with anions from a sulfur oxy-acid or salt thereof, in the presence of strong acid of $-H_o$ greater than 7.0. Evidence for the formation of ionic sulfonates in the reaction of a rhodium compound with a sulfur oxy-acid is provided hereinafter in Example 30. Further evidence is provided in the Procedure for Catalyst Preparation using Nafion ® Perfluorosulfonic Acid Resin described below wherein a reaction between rhodium trichloride and the polymeric sulfonic acid is followed by titration of the liberated hydrochloric acid and by analysis of rhodium chemically bound to the polymer. Other examples summarized in Table 3, infra, confirm the operability of the metal salts of sulfur oxy-acids and the requirement of strong acid in combination with the Group VIII metal sulfur-oxy compound as the catalyst in the oxidative carbonylation process of the invention.

As already suggested, the Group VIII metal compound which is used as catalyst ingredient (a) can be any Group VIII metal compound capable of combining chemically with a sulfur oxy-acid or its metal salt. Examples of such compounds include the rhodium acetate, trifluoroacetate, chloride and nitrate, the rhodium carbonyls $Rh_6(CO)_{16}$ and $RhH(CO)(P\phi_3)_3$, where $\phi$ is phenyl, iridium chloride, ruthenium chloride, platinum chloride, osmium chloride and palladium nitrate. Examples of suitable sulfur oxy-acids include sulfuric acid; oleum; fluorosulfonic acid; α-fluorosulfonic acids, including trifluoromethanesulfonic acid (triflic acid), perfluorooctanesulfonic acid, and $CF_3CF_2OCF_2CF(CF_3)OCF_2CF_2SO_3H$ (perfluoro-4-methyl-3,6-dioxaoctanesulfonic acid); methanesulfonic acid; benzenesulfonic acid; and p-toluenesulfonic acid. Examples of acids suitable for use as catalyst component (c) include the above sulfur oxy-acids which have an $-H_o$ of greater than 7.0, hydrofluoric acid and mixtures of hydrofluoric acid and antimony pentafluoride. Such acids are described further by Olah et al. in Science, 206, 13 (1979).

Preferred catalysts in the process of this invention provide toluic acids, at least 70 mol % of which is p-toluic acid, and include those wherein catalyst ingredient (a) is a compound of rhodium, iridium or ruthenium. Especially preferred catalysts provide toluic acids, at least 85 mol % of which is p-toluic acid, and include those wherein catalyst ingredient (a) is a compound of rhodium or iridium and catalyst ingredients (b) and (c) are the same and consist of a sulfur oxy-acid having an $-H_o$ greater than 7.0.

Sufficiently strong, that is, having an $-H_o$ of greater than 7.0, polymeric sulfonic acids also can be used in the process of the invention. Such acids are comprised of polymeric materials having sulfonic acid groups attached to the polymer structure. Representative of such a sulfonic acid is a perfluorinated polymeric sulfonic acid. Nafion ® Perfluorosulfonic Acid Products represent commercially available materials of this type. The use of Nafion ® as a strong acid is described in J. Org. Chem., 42, 4187 (1977) and 43, 3142 and 3147 (1978) in a series of papers by Olah et al. and Kaspi et al. and entitled "Heterogeneous Catalysis By Solid Superacids." It should be understood that the polymeric sulfonic acids useful in this invention normally provide catalyst ingredients (b) and (c). If, however, the sulfonic acid sites in the polymer have been largely or completely neutralized, i.e., converted to the salt form by the addition of a salt or hydroxide of a Group Ia or IIa metal (see below and Table 1), only catalyst ingredient (b) is provided by the polymer and a strong acid ingredient (c) must be added to obtain an operable catalyst. It will be obvious to one skilled in the art that when at least 0.5 mol % of the sulfonic acid or sulfonate salt sites in the polymer have reacted with the catalytically active Group VIII metal ions, catalyst ingredient (a) is also provided by the polymer. Catalysts prepared herein from a polymeric sulfonic acid are referred to as heterogeneous catalysts. Those prepared herein from the nonpolymeric sulfonic acid are referred to as homogeneous catalysts.

Included in this invention are perfluorinated polymeric sulfonic acids having, based on the sulfonic acid groups, about 5 to 98.5 mol % of hydrogen ions and 1.5 to about 95 mol % of rhodium, iridium, ruthenium, platinum, palladium or osmium ions. Preferred polymeric sulfonic acids have 50 to 98.5 mol % of the hydrogen ions and 1.5 to 50 mol % of the Group VIII metal ion. Also included in this invention are perfluorinated polymeric sulfonate salts having, based on the sulfonate groups, about 5 to 98.5 mol % of Group Ia or Group IIa metal ions and 1.5 to about 95 mol % of rhodium, iridium, ruthenium, platinum, palladium or osmium ions.

The process of the invention is carried out at 110°–250° C., preferably 130°–200° C. At below 110° C. the reaction proceeds, but at slow rates. There is little, if any, advantage in operating the process above 250° C. Particularly if any catalyst component is a thermally unstable material, for example, as are some polymeric sulfonic acids, the upper limit of reaction temperature must be selected accordingly.

Although the reaction pressure is not critical to the process of the invention, generally it should be at least 500 psi (3.45 MPa). The upper limit of pressure is usually governed by the cost of the equipment needed to contain the reactant materials.

Preferably, in order to avoid the use and handling of an explosive reaction mixture, the amount of oxygen introduced into the system should not exceed 7.5 mol % of the combined amounts of carbon monoxide and oxygen in the system. If the reaction is carried out in a batch type operation, for example, in an autoclave, it may be desirable, in order to maintain the lowest possible level of oxygen, to introduce the initial charge of toluene and carbon monoxide before adding the oxygen. Carbon monoxide can then be added subsequently in such amounts as is necessary to maintain the desired reaction pressure as carbonylation takes place.

As is already evident from the above description, the reaction can be carried out in a batchwise or continuous mode of operation in a system which can be either homogeneous or heterogeneous, depending on whether or not the catalyst is soluble in the reaction medium. Although a solvent or liquid medium which is inert to oxidative carbonylation can be present during the reaction, it is not necessary in the process of the invention since the toluene itself serves as a solvent or liquid medium. Workup of the toluic acid from the reaction mixture can be carried out by conventional means. Heterogeneous catalyst can be removed by filtration of the reaction mixture. When a soluble catalyst is used, that is, when the system is homogeneous, the reaction mixture can be diluted with methylene chloride and extracted with aqueous sodium chloride, after which the methylene chloride layer can be evaporated to recover the toluic acid.

EXAMPLES

In the following examples, the toluic acids which were produced were converted to trimethylsilyl esters by conventional techniques and then analyzed by means of standard gas chromatographic procedures.

PROCEDURE FOR CATALYST PREPARATION USING NAFION ® PERFLUOROSULFONIC ACID RESIN

The heterogeneous catalysts were prepared by stirring an aqueous solution of a soluble compound of an above-listed Group VIII metal (for example, the nitrate or chloride) with Nafion ® (H+) (of equivalent weight 1100) either until the supernatant of the resultant slurry was colorless or for such time as was necessary to convert the desired number of acidic sites in the Nafion ® (H+) to the Group VIII metal salt. The formation of the Group VIII metal salt can be followed by titrating the acid (for example, nitric acid or hydrochloric acid) liberated in the supernatant of the slurry. A specific example of the procedure follows.

Forty-five g of Nafion ® (H+) containing 41 mmols of sulfonic acid groups in 450 ml of $H_2O$ was stirred with 0.78 g of $RhCl_3.xH_2O$ (x is about 3) at 95° C. for about 100 h. The resultant slurry was filtered and the orange resin was dried in a vacuum oven for about 3 h at about 100° C. The filrate was titrated for liberated hydrochloric acid (6.3 mmols of HCl), and the resin was analyzed for rhodium (0.47 wt % Rh, corresponding to 2.0 mmols of Rh). The catalyst thus prepared contains $$\frac{2.0 \times 100}{2.0 + (41 - 6.3)} = 5.4 \text{ mol \% rhodium ions, and}$$

-continued $$\frac{(41 - 6.3)100}{(41 - 6.3) + 2.0} = 94.6 \text{ mol } \% \text{ hydrogen ions.}$$

The mold % (a) of rhodium compound in the catalyst ingredients, as calculated by the formula given above Table 1, is $$\text{mol } \% (a) = \frac{3.0 \times 100}{41 + 3.0} = 6.8 \text{ mol } \% \text{ rhodium compounds.}$$

Nafion ® (H+) may be converted to a salt form, e.g., the Na salt, by a similar procedure wherein the resin is treated with an aqueous solution of sodium chloride or sodium nitrate. The salt form may be further treated with a water-soluble rhodium, iridium, platinum, ruthenium, palladium or osmium compound to replace the desired number of Na ions with the Group VIII metal ion.

Alternatively, Nafion ® (H+) may be converted substantially to the Group VIII metal salt by either of the above techniques, and an appropriate strong acid may be added to provide the necessary catalyst ingredients (b) and/or (c), as discussed above.

PROCEDURE FOR SHAKER TUBE EXPERIMENT WITH HETEROGENEOUS CATALYST FROM NAFION ®

In a typical experiment, a shaker tube was flushed with $N_2$, charged with the catalyst prepared as described above, cooled, evacuated and charged with 120 ml of toluene. The tube was sealed and heated to reaction temperature. Carbon monoxide, then oxygen, and then more carbon monoxide was introduced into the tube until the desired pressure was reached. The mol fraction of oxygen was 0.075. During the reaction time of two hours, the tube was repressurized with carbon monoxide as necessary to maintain pressure during carbonylation. After the tube was discharged, the catalyst was removed by filtration and the filtrate was analyzed for toluic acids.

PROCEDURE FOR SHAKER TUBE EXPERIMENT WITH HOMOGENEOUS (SOLUBLE) CATALYST

In a typical experiment, a shaker tube is flushed with $N_2$, charged with an appropriate Group VIII metal compound (a), cooled, evacuated and charged with a suitable sulfur oxy-acid or metal salt thereof (b), a suitable acid or acid mixture having an $-H_o$ of greater than 7.0 (c), and, finally, 80 ml of toluene. Alternatively, the Group VIII metal compound can be reacted separately with excess sulfur oxy-acid or metal salt thereof and then charged to the shaker tube in place of the first two ingredients described above. After being charged the tube is sealed and heated to reaction temperature. Carbon monoxide, then oxygen, and then more carbon monoxide is introduced into the tube until the desired pressure is reached. The mol fraction of oxygen is no greater than 0.075. During the reaction time of two hours, the tube is repressurized with carbon monoxide as necessary to maintain pressure during carbonylation. The tube is discharged of the liquid contents. The solution is diluted with $CH_2Cl_2$ and extracted with saturated aqueous NaCl solution. The organic phase is dried over MgSO$_4$, concentrated to a small volume, and then analyzed for toluic acids.

EXAMPLE 1-29

These examples represent various embodiments of the process of the invention, carried out using the procedures outlined above. Appropriate data for the examples using the heterogeneous catalyst are summarized in Table 1, for the examples using the homogeneous catalyst, in Tables 2 and 3. At the end of each table are provided data relative to experimental showings (S) which were carried out to compare the process of the invention as claimed herein with similar processes outside the invention.

For the heterogeneous systems, Experiments S1 and S2 (Table 1) show that no reaction occurs when the catalyst lacks ingredient (a). S5 shows that ingredient (c) is also essential for reaction. S3 and S4 illustrate the importance of oxygen and sufficiently high temperature in the process of this invention.

For the homogeneous systems, Experiments S6–S11 (Table 2) show that catalyst ingredient (b) is essential for reaction. S6–S8 also lack ingredient (c), as do S13 and S14 (Table 3); acetic, trifluoroacetic and hydrochloric acids do not meet the requirements of ingredient (c) as defined above. S12 confirms that ingredient (a) is essential for reaction.

The difference between the mol % Group VIII metal compound (col. 4 of Tables 1–3), i.e., the amount of catalyst ingredient (a), and 100 mol % represents the mol % of catalyst ingredients (b)+(c). In Exanples 1–24 (Tables 1 and 2), ingredients (b) and (c) are provided by the same compound; in Examples 25–29 (Table 3), mol % of ingredient (b), i.e., CF$_3$SO$_3$Na, is listed.

The mol % of Group VIII metal compound in the catalyst ingredients is calculated using the formula $$\text{mol } \% (a) = \frac{\text{mols of } (a)}{\text{mols of } (a + b + c)} \times 100$$

where (a), (b) and (c) are the catalyst ingredients defined as above.

The experiments which are summarized in Table 3 were carried out at 150° C. and 27.6 mPa.

TABLE 1

| Heterogeneous Catalyst | | | | | | | |
|---|---|---|---|---|---|---|---|
| No. | Prepared Catalyst Wt (g) | Resin Compd Form | Mol % Rh | Temp (°C.) | P (MPa) | Mol % Isomer Distribution | | |
| | | | | | | o | m | p |
| 1 | 4 | H+ | 6.3 | 150 | 27.6 | 1 | 7 | 92 |
| 2 | 3 | H+ | 9.5 | 120 | 27.6 | 0.1 | 8.4 | 91.5 |
| 3 | 7.4 | H+ | 6.8 | 150 | 34.5 | 0.7 | 5.7 | 93.6 |
| 4 | 4 | H+ | 12.9 | 150 | 13.8 | 9.8 | 8.5 | 90.7 |
| 5 | 4 | H+ | 12.9 | 150 | 6.9 | 0.8 | 9.2 | 90 |
| 6 | 4 | H+ | 12.7 | 150 | 3.45 | 1.2 | 8.7 | 90 |
| 7 | 4 | H+ | 12.9 | 150 | 27.6 | 1 | 8 | 91 |
| 8 | 4 | H+ | 14.5 | 150 | 27.6 | 1.5 | 12.5 | 86 |
| 9 | 4 | H+ | 25.3 | 150 | 27.6 | 1.6 | 12.7 | 85.7 |
| S1 | 4 | H+ | 0 | 150 | 27.6 | Nil | Nil | Nil |
| S2 | 4 | Na+ | 0 | 150 | 27.6 | Nil | Nil | Nil |
| S3 | 4 | H+ | 12.9 | 150 | 27.6* | Nil | Nil | Nil |
| S4 | 4 | H+ | 12.9 | 100 | 27.6 | [← | trace | →] |
| S5 | 4 | Na+ | 6.2 | 150 | 27.6 | Nil | Nil | Nil |

*without oxygen

TABLE 2

| Ex. No. | Catalyst Components | Homogeneous Catalyst Group VIII Metal Compd Wt (g) | Mol % Group VIII Compd Metal | Temp. (°C.) | P (MPa) | Mol % Isomer Distribution o | m | p |
|---|---|---|---|---|---|---|---|---|
| 10 | $RhCl_3/CF_3SO_3H$ | 0.3 | 4.8 | 150 | 27.6 | 1.9 | 5.7 | 92.4 |
| 11 | $Rh(NO_3)_3/CF_3SO_3H$ | 0.1 | 2.8 | 150 | 27.6 | 0.6 | 6.0 | 93.0 |
| 12 | $Rh(NO_3)_3/CF_3SO_3H$ | 0.3 | 4.2 | 150 | 16.6 | 3.2 | 6.2 | 90.7 |
| 13 | $Rh(NO_3)_3/C_8F_{17}SO_3H$ | 0.1 | 3.2 | 150 | 27.6 | 0.5 | 8.5 | 91.0 |
| 14 | $Rh(NO_3)_3/CF_3CF_2OCF_2\text{—}$ $\underset{CF_3}{\overset{|}{C}}FOCF_2CF_2SO_3H$ | 0.3 | 8.6 | 150 | 27.6 | 2.7 | 5.8 | 92.0 |
| 15 | $Rh(NO_3)_3/CH_3SO_3H$ | 0.2 | 2.1 | 150 | 27.6 | 1.4 | 6.2 | 92.4 |
| 16 | $Rh(NO_3)_3/FSO_3H$ | 0.2 | 1.9 | 150 | 27.6 | 0.6 | 4.8 | 94.5 |
| 17 | $Rh(NO_3)_3/H_2SO_4$ | 0.2 | 1.7 | 150 | 27.6 | 0.7 | 7.3 | 92.0 |
| 18 | $Rh(NO_3)_3/p\text{-}CH_3C_6H_4SO_3H$ | 0.2 | 6.3 | 150 | 27.6 | 2.2 | 8.4 | 89.3 |
| 19 | $Rh(NO_3)_3/C_6H_5SO_3H$ | 0.3 | 3.5 | 150 | 27.6 | 1.0 | 8.4 | 90.6 |
| 20 | $Rh_6(CO)_{16}/CF_3SO_3H$ | 0.5 | 2.0 | 150 | 27.6 | 1.5 | 7.5 | 91.0 |
| 21 | $Rh_6(CO)_{16}/CH_3SO_3H$ | 0.4 | 1.2 | 150 | 27.6 | 0.6 | 7.8 | 91.6 |
| 22 | $RhH(CO)(P\phi_3)_3/CF_3SO_3H$ | 1.0 | 4.6 | 150 | 27.6 | 1.7 | 11.9 | 86.4 |
| 23 | $[Rh(O_2CCH_3)_2]_2/CF_3SO_3H$ | 0.4 | 3.8 | 150 | 27.6 | 2.0 | 9.0 | 89.0 |
| 24 | $PtCl_2/CF_3SO_3H$ | 0.3 | 4.9 | 150 | 27.6 | 15.0 | 20.0 | 65.0 |
| S6 | $[Rh(O_2CCH_3)_2]_2/CH_3CO_2H$ | 0.3 | 1.9 | 150 | 27.6 | Nil | Nil | Nil |
| S7 | $[Rh(O_2CCF_3)_2]_2/CF_3CO_2H$ | 0.3 | 1.6 | 150 | 27.6 | Nil | Nil | Nil |
| S8 | $Rh(NO_3)_3/CF_3CO_2H$ | 0.3 | 0.7 | 150 | 27.6 | Nil | Nil | Nil |
| S9 | $RhCl_3/HF$ | 0.3 | 1.1 | 150 | 27.6 | Nil | Nil | Nil |
| S10 | $RhCl_3/SbF_5*/HF*$ | 0.3 | 1.0 | 150 | 27.6 | Nil | Nil | Nil |
| S11 | $Rh(NO_3)_3/HF$ | 0.3 | 0.9 | 150 | 27.6 | Nil | Nil | Nil |
| S12 | $CF_3SO_3H$ | 0 | 0 | 150 | 27.6 | Nil | Nil | Nil |

*0.00922 mol $SbF_5$, 0.1 mol HF

TABLE 3

| Ex. No. | Catalyst Components | Homogeneous Catalyst Group VIII Metal Compd. wt (g) | Mol % Group VIII Compd Metal | Mol % $CF_3SO_3Na$ | Mol % Isomer Distribution o | m | p |
|---|---|---|---|---|---|---|---|
| 25 | $Rh(NO_3)_3/CF_3SO_3Na/HF$ | 0.3 | 0.9 | 4.9 | 1.7 | 14.6 | 83.7 |
| 26 | $Rh(NO_3)_3/CF_3SO_3Na/SbF_5*/HF*$ | 0.3 | 0.9 | 4.9 | 1.5 | 11.5 | 87.0 |
| 27 | $IrCl_3/CF_3SO_3Na/CF_3SO_3H$ | 0.4 | 4.5 | 19.6 | 1.2 | 11.0 | 87.8 |
| 28 | $Pd(NO_3)_2/CF_3SO_3Na/CF_3SO_3H$ | 0.4 | 5.2 | 16.2 | 32.0 | 16.0 | 52.0 |
| 29 | $RuCl_3/CF_3SO_3Na/CF_3SO_3H$ | 0.4 | 6.3 | 19.2 | 10.0 | 18.0 | 72.0 |
| S13 | $Rh(NO_3)_3/CF_3SO_3Na/HCl$ | 0.3 | 14.9+ | 85.0 | Nil | Nil | Nil |
| S14 | $Rh(NO_3)_3/CF_3SO_3Na$ | 0.3 | 24.0+ | 76.0 | Nil | Nil | Nil |

*0.00922 mol $SbF_5$, 0.1 mol HF

+calcd as mol % Rh = $\dfrac{\text{mols Rh compound}}{\text{mols (Rh + CF}_3\text{SO}_3\text{Na)}} \times 100$

EXAMPLE 30

A sample of $Rh(OH)_3H_2O$, prepared from $RhCl_3.3H_2O$ by the procedure of Basolo, Inorganic Syntheses, VII, page 214, was reacted without external heating with a 3:1 molar excess of trifluoromethanesulfonic acid. Unreacted acid was distilled off under reduced pressure and a reddish-brown solid was recovered. Infrared analysis of the solid showed characteristic bands at 1250 cm$^{-1}$, 1176 cm$^{-1}$ and 1030 cm$^{-1}$, closely, similar to the trifluoromethanesulfonate ion ($CF_3SO_3^-$) bands observed in various metal salts of trifluoromethanesulfonic acid by Gramstad and Haszeldine, J. Chem. Soc., 173 (1956), Haszeldine & Kidd, J. Chem. Soc., 4228 (1954), and Batchelor et al., Inorg. Chem., 16, 1414 (1977).

0.3 g of the rhodium trifluoromethanesulfonate product prepared above was substituted for the rhodium or iridium compound and the sulfur oxy-acid in the procedures outlined for Examples 1-29. In one experiment, (i), no acid was added; in second and third experiments (ii) and (iii), trifluoroacetic acid and trifluoromethanesulfonic acid, respectively, were added in such amounts that the mixtures of rhodium compound and acid contained: (ii) 2.0 mol % rhodium compound, 98.0 mol % trifluoroacetic acid; and (iii) 2.4 mol % rhodium compound, 97.6 mol % trifluoromethanesulfonic acid. Both experiments were run at 150° C. and 27.6 MPa with the following results being obtained:

TABLE 4

| | Mol % Isomer Distribution | | |
|---|---|---|---|
| | o | m | p |
| (i) | Nil | Nil | Nil |
| (ii) | Nil | Nil | Nil |
| (iii) | 2.0 | 9.0 | 89.0 |

EXAMPLE 31

A 300 cc Hastelloy C autoclave equipped with separate gas and liquid inlet lines, thermocouple, stirrer, cooling coils and an overflow dip tube was charged with 125 ml of toluene and 30 g of Nafion ® ($H^+$, $Rh^{+3}$) (10.4 mol % metal cation). The autoclave was heated to 150° C. and pressured to 4000 psi (27.6 MPa) with a gaseous mixture of oxygen and carbon monoxide (mol % of $O_2$ is 3%). Toluene and the gaseous mixture were fed at a rate of 3.0 ml/min and 2200 cc/min, respectively. Product was continuously discharged through the dip tube and through a gas-liquid separator, and the liquid was collected. During the four hours of operation, the stirring rate was maintained at 500 RPM. Analysis of the collected liquid showed the presence of 94.4% of the p-toluic acid isomer. The conversion of toluene was 1%.

EXAMPLE 32

A. Preparation of Palladium-Exchanged Nafion ® ($H^+$) Resin

Twenty two g of Nafion ® ($H^+$) containing 20.0 mmols of sulfonic acid groups in 300 ml of $H_2O$ was stirred with 2.63 g of $Pd(NO_3)_2 \cdot xH_2O$ (39.0 wt % Pd; 9.7 mmols of Pd) at 60° C. for about 5 h. The resultant slurry was filtered and the reddish-brown resin was dried in a vacuum oven for about 5 h at about 110° C. The clear filtrate was titrated for liberated nitric acid (18.5 mmols of $HNO_3$), and the resin was analyzed for palladium (3.95 wt % Pd, corresponding to 8.5 mmols of Pd). Mol % of palladium in the resin composition was:

$$\frac{8.5 \times 100}{8.5 + (20.0 - 18.5)} = 85.0 \text{ mol \%}.$$

Hydrogen ions comprised the remainder (15.0 mol %), the total amounting to 100 mol %. The mol % of palladium compound in the starting ingredients (to prepare the resin) was:

$$\frac{9.7 \times 100}{20.0 + 9.7} = 32.7 \text{ mol \%}.$$

B. Preparation of Heterogeneous Catalyst and Toluic Acid

A palladium-exchanged Nafion ® ($H^+$) resin was prepared as in Part A and contained at least 95 mol % palladium. Eight g of this resin containing 4.3 mmols of palladium, 6.76 g (45.0 mmols) of trifluoromethanesulfonic acid, and 80 ml of toluene were charged to a shaker tube previously flushed with nitrogen. The tube was pressurized with 200 psi (1.38 MPa) of a mixture of CO and $O_2$ (3 mol % $O_2$), and the temperature was increased to 150° C. A total pressure of 4000 psi (27.6 MPa) was reached by continuing to pressurize the shaker tube to 800 psi (5.5 MPa) with a $CO/O_2$ mixture, followed by 180 psi (1.24 MPa) oxygen and 3020 psi (20.8 MPa) of a $CO/O_2$ mixture. During the reaction time of two hours, the tube was repressurized with a $CO/O_2$ mixture as necessary to maintain pressure. After the reaction, the tube was discharged, the resin was removed by filtration and the filtrate was diluted with methylene chloride and washed with water. The organic phase was dried over $MgSO_4$, evaporated to a small volume, and analyzed for toluic acids with the following results:

| Mol % Isomer Distribution | | |
|---|---|---|
| o | m | p |
| 29.0 | 16.0 | 55.0 |

The mol % of Pd compound in the catalyst ingredients was $$\frac{3.5 \times 100}{3.5 + 7.3 + 45.0} = 6.3 \text{ mol \%}.$$

The experiment described above was repeated except that trifluoromethanesulfonic acid was omitted. Toluic acids were formed in approximately 3% of the amount obtained above.

| Mol % Isomer Distribution | | |
|---|---|---|
| o | m | p |
| 34.0 | 27.0 | 39.0 |

EXAMPLE 33

Twenty-two g of Nafion ® ($H^+$) containing 20.0 mmols of sulfonic acid groups in 300 ml of $H_2O$ was stirred with 2.2 g of $Rh(NO_3)_3 \cdot 2H_2O$ (6.8 mmols) at 60° C. for about 67 h. The resultant slurry was filtered and the orange resin was dried in a vacuum oven for about 5 h at about 110° C. The filtrate was titrated for liberated nitric acid (5.6 mmols) and the resin was analyzed for rhodium (2.6 mmols). The results show that the catalyst composition contained 15.3 mol % rhodium ions and 84.7 mol % hydrogen ions. The mol % of rhodium compound in the catalyst ingredients was 25.4 mol % (Compare Example 9, Table 1, wherein the mol % Rh was 25.3).

BEST MODE FOR CARRYING OUT THE INVENTION

The best mode for carrying out the process of the invention is believed to be demonstrated by Examples 3 and 11 (batchwise) and 31 (continuous).

INDUSTRIAL APPLICABILITY

Toluic acid, particularly p-toluic acid, is a useful intermediate in the preparation of terephthalic acid which is used in the manufacture of fiber-forming polyesters.

Although the preferred embodiments of the invention have been illustrated and described, it is to be understood that there is no intent to limit the invention to the precise consructions herein disclosed and that the right is reserved to all changes and modifications within the scope of the invention as defined in the appended claims.

I claim:

1. Perfluorinated polymeric sulfonic acid having, based on the sulfonic acid groups, about 5 to 98.5 mol % of hydrogen ions and 1.5 to about 95 mol % of rhodium, iridium, ruthenium, platinum, palladium or osmium ions.

2. Perfluorinated polymeric sulfonic acid having, based on the sulfonic acid groups, 50 to 98.5 mol % of hydrogen ions and 1.5 to 50 mol % of rhodium, iridium, ruthenium, platinum, palladium or osmium ions.

3. Perfluorinated polymeric sulfonate salt having, based on the sulfonate groups, about 5 to 98.5 mol % of Group Ia or Group IIa metal ions and 1.5 to about 95 mol % of rhodium, iridium, ruthenium, platinum, palladium or osmium ions.

* * * * *